United States Patent
Mavely et al.

(10) Patent No.: US 11,491,107 B2
(45) Date of Patent: Nov. 8, 2022

(54) MUCOADHESIVE PREPARATIONS, METHODS AND APPLICATIONS THEREOF

(71) Applicant: AXIO BIOSOLUTIONS PVT. LTD., Ahmedabad (IN)

(72) Inventors: Leo Mavely, Bangalore (IN); Kiran Sonaje, Bangalore (IN); Indu A. G., Bangalore (IN)

(73) Assignee: AXIO BIOSOLUTIONS PVT. LTD., Gujarat (IN)

( * ) Notice: Subject to any disclaimer, the term of this patent is extended or adjusted under 35 U.S.C. 154(b) by 399 days.

(21) Appl. No.: 16/347,246

(22) PCT Filed: Nov. 3, 2017

(86) PCT No.: PCT/IB2017/056871
§ 371 (c)(1),
(2) Date: May 3, 2019

(87) PCT Pub. No.: WO2018/083643
PCT Pub. Date: May 11, 2018

(65) Prior Publication Data
US 2019/0254956 A1    Aug. 22, 2019

(30) Foreign Application Priority Data
Nov. 4, 2016  (IN) .............................. 201621037801

(51) Int. Cl.
| | | |
|---|---|---|
| *A61K 9/00* | (2006.01) |
| *A61P 1/02* | (2006.01) |
| *A61K 9/19* | (2006.01) |
| *A61K 47/12* | (2006.01) |
| *A61K 47/36* | (2006.01) |
| *A61K 31/155* | (2006.01) |
| *A61K 31/167* | (2006.01) |
| *A61F 13/00* | (2006.01) |

(52) U.S. Cl.
CPC ............ *A61K 9/006* (2013.01); *A61K 9/0043* (2013.01); *A61K 9/0063* (2013.01); *A61K 9/19* (2013.01); *A61K 47/12* (2013.01); *A61K 47/36* (2013.01); *A61P 1/02* (2018.01); *A61F 13/00063* (2013.01); *A61K 31/155* (2013.01); *A61K 31/167* (2013.01)

(58) Field of Classification Search
None
See application file for complete search history.

(56) References Cited

U.S. PATENT DOCUMENTS

| | | | | |
|---|---|---|---|---|
| 4,837,285 A | * | 6/1989 | Berg ......................... | A61K 9/70 128/DIG. 8 |
| 2006/0089584 A1 | | 4/2006 | McAdams et al. | |
| 2006/0159732 A1 | * | 7/2006 | Cullen .................... | A61L 15/46 424/445 |
| 2008/0050398 A1 | * | 2/2008 | Bockmuehl ........ | A61K 38/1709 424/190.1 |

OTHER PUBLICATIONS

Loke et al., Wound Dressing with Sustained Anti-Microbial Capability, J Biomed Mater Res (Appl Biomater) 53: 8-17, 2000 (Year: 2000).*
International Searching Authority, "International Search Report," Issued In connection with International Patent Application No. PCT/IB2017/056817, dated Feb. 8, 2018.
International Searching Authority, "Written Opinion," issued in connection with International Patent Application No. PCT/IB2017/056817, dated Feb. 8, 2018.
Cafaggi et al., "Preparation and evaluation of nanoparticles made of chitosan or N-trimethyl chitosan and a cisplatin-alginate complex," Journal of Controlled Release, vol. 120, Nos. 1 -2, Aug. 16, 2007, pp. 110-123.

* cited by examiner

*Primary Examiner* — Jennifer A Berrios
(74) *Attorney, Agent, or Firm* — Foley & Lardner LLP

(57) ABSTRACT

The present disclosure relates to mucoadhesive preparation comprising chitosan, and methods thereof. Further, the present disclosure relates to applications of the mucoadhesive preparation.

17 Claims, 10 Drawing Sheets

Buccal patch

Nasal administration

Oral administration

Throat/ respiratory administration

MUCOADHESIVE PREPARATIONS, METHODS AND APPLICATIONS THEREOF

RELATED APPLICATIONS

The present application claims priority under 37 U.S.C. § 371 to International Patent Application No. PCT/IB2017/056871, filed Nov. 3, 2017, which claims priority to and the benefit of Indian Patent Application No. 201621037801, filed on Nov. 4, 2016. The contents of these applications are hereby incorporated by reference in their entireties.

TECHNICAL FIELD

The present disclosure relates to the field of biotechnology and drug delivery in general. Particularly, the disclosure relates to mucoadhesive preparation and methods thereof. Further, the present disclosure relates to applications of the mucoadhesive preparation.

BACKGROUND OF THE DISCLOSURE

Various mucosal surfaces, such as those in oral, nasal, ocular, vaginal and rectal cavities have been widely investigated for the mucosal as well as the trans-mucosal delivery of active pharmaceuticals, where the aim is to achieve a site-specific, localized delivery of the drug on the mucosa and systemic absorption of drugs through the mucosal barrier. The barrier properties of the mucosal epithelium pose a challenge to the drug absorption. Furthermore, the limited absorption area and physiological mechanisms that wash the formulation away from the absorption site hamper both the local as well as systemic drug delivery.

Generally, the dosage forms intended for mucosal drug delivery should be small and flexible enough to effortlessly fit in the site without causing any discomfort or irritation to the patients. Other desired characteristics include high drug loading capacity, controlled drug release, good mucoadhesive properties, smooth surface, tastelessness, and convenient application. Given this scenario, various technologies ranging from fast dissolving films to mucoadhesive gels and patches have been investigated for the mucosal drug delivery. The fast dissolving films offer improved mechanical properties over the conventional orally disintegrating tablets and lozenges; but they are only suited for short duration applications. A number of mucoadhesive materials such as chitosan have been reported in the literature.

Chitosan is a well-known natural polymer and several of its mucoadhesive preparations have been reported such as gels/hydrogels, nano/microparticles, films and tablets. Chemically, chitosan is a linear polysaccharide consisting of randomly distributed glucosamine and N-acetyl glucosamine units. The primary amine in the glucosamine units of chitosan undergoes protonation in acidic pH and renders a highly cationic charge to the chitosan chains. The cationic charge of chitosan is necessary for many of its medically relevant characteristics such as mucoadhesion and bioadhesion. The pKa of primary amines in chitosan is 6.5 and therefore they deprotonate (lose cationic charge) at pH >6.5. Since the pH of mucosal secretions and surfaces is generally close to pH 7.4, conventional chitosan preparations lose their mucoadhesive properties under such conditions. To overcome this problem, several researchers have reported chemically modified chitosan derivatives such as trimethyl chitosan derivatives which can improve mucoadhesive characteristics of chitosan by quaternization of the amine groups. However, this approach increases the cost of the raw materials and makes the product commercially impractical. Besides, unmodified chitosan also benefits from the proven safety and toxicity which makes its regulatory approval easy. Therefore, mucoadhesive preparations of unmodified chitosan which present sufficient mucoadhesive characteristics even at physiological pH values are desirable.

Another disadvantage with the conventional chitosan formulations such as films, patches, tablets or powders is that they suffer from inadequate mucoadhesion and shorter residence time at the application sites. This happens due to the charge neutralization of chitosan molecules by physiological secretions. Additionally, conventional chitosan formulations such as films or lyophilized matrix usually absorb fluids and show swelling characteristics. However, fluid absorption and swelling is disadvantageous for prolonged mucoadhesion of the drug delivery system. The fluid absorption and swelling leads to rapid release of drugs, the drug delivery system in the form of a patch becomes bulky which may be uncomfortable for patients (e.g in buccal cavity). The patch may also get dislodged from the adhesion site due to increased weight after swelling.

Additionally, the chitosan films and hydrogels require usage of harsh chemical crosslinking agents to improve their stability in mucosal fluids, which in turn adversely affects their mucoadhesive characteristics. Further, the mucoadhesive nano/microparticles of unmodified chitosan obtained using conventional methods may prematurely release the drug in the lumen and give low systemic bioavailability. Additionally, the conventional mucoadhesive patches prepared by solvent casting method or compression (like tablets) may also damage the thermally unstable drugs such as proteins and peptides.

Thus, the present disclosure overcomes the drawbacks of the prior art by providing for efficient mucoadhesive preparations and methods thereof.

STATEMENT OF THE DISCLOSURE

Accordingly, the present disclosure relates to a mucoadhesive preparation comprising chitosan and optionally comprising an organic acid; wherein the mucoadhesive preparation is in a compressed form; a method of obtaining a mucoadhesive preparation, said process comprising acts of contacting chitosan with organic acid, to obtain a chitosan solution, subjecting the chitosan solution to lyophilisation to obtain dry chitosan sponge, and compressing the dry chitosan sponge to obtain a mucoadhesive preparation; use of mucoadhesive preparation as drug delivery system; use of a mucoadhesive preparation in treatment of mucosal disorder; a drug delivery system for delivering a drug to a patient in a sustained and controlled manner, the system comprising mucoadhesive preparation and a drug; a method of delivering one or more drug to a subject in need thereof, wherein the method comprises application of the drug delivery system on mucosal surface of the subject.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a description below are incorporated in and form part of the specification, and serve to further illustrate the embodiments and explain various principles and advantages, in accordance with the present disclosure where:

FIG. 1 depicts the schematic diagram showing the mechanism for the enhanced mucoadhesion of chitosan preparations of the present disclosure.

FIGS. 2 (a), 2 (b) and 2 (c) depict the parameters of different lyophilisation processes employed in the present disclosure for preparation of porous chitosan matrix.

FIGS. 3(a) and 3(b) depict scanning electron microscopic images showing the porous structure of the lyophilized drug-free chitosan matrix before compression.

Figure 6:
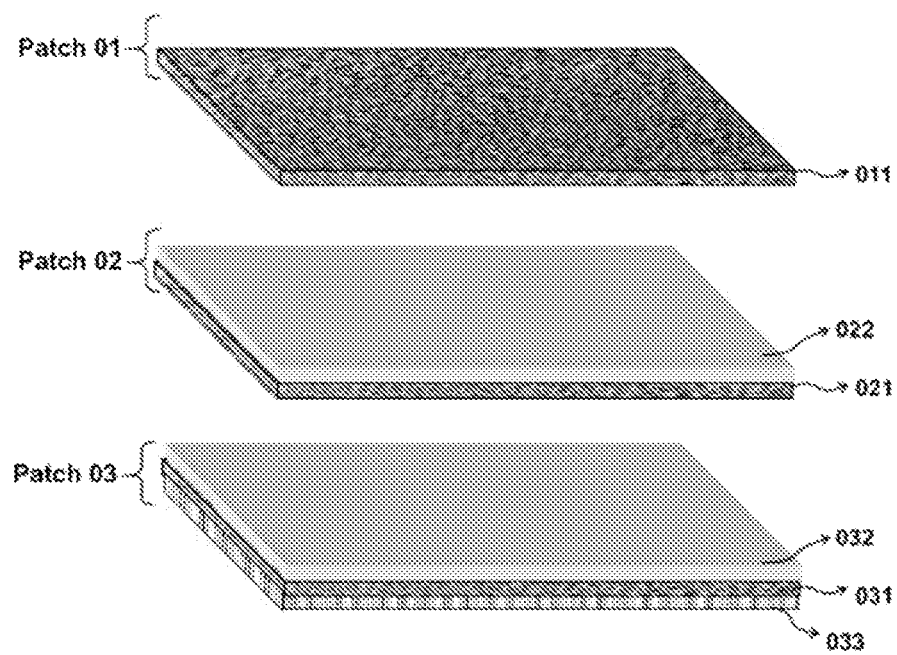

FIG. 6 depicts the various design configurations of the mucoadhesive patches; wherein Patch 01 is drug-loaded mucoadhesive patch in single layer (011); Patch 02 contains a water impermeable backing layer (022) over a drug containing mucoadhesive layer (021); Patch 03 contains a drug containing layer (031) sandwiched between impermeable backing layer (032) on top and drug-free adhesive layer (033) on bottom.

Figure 7:
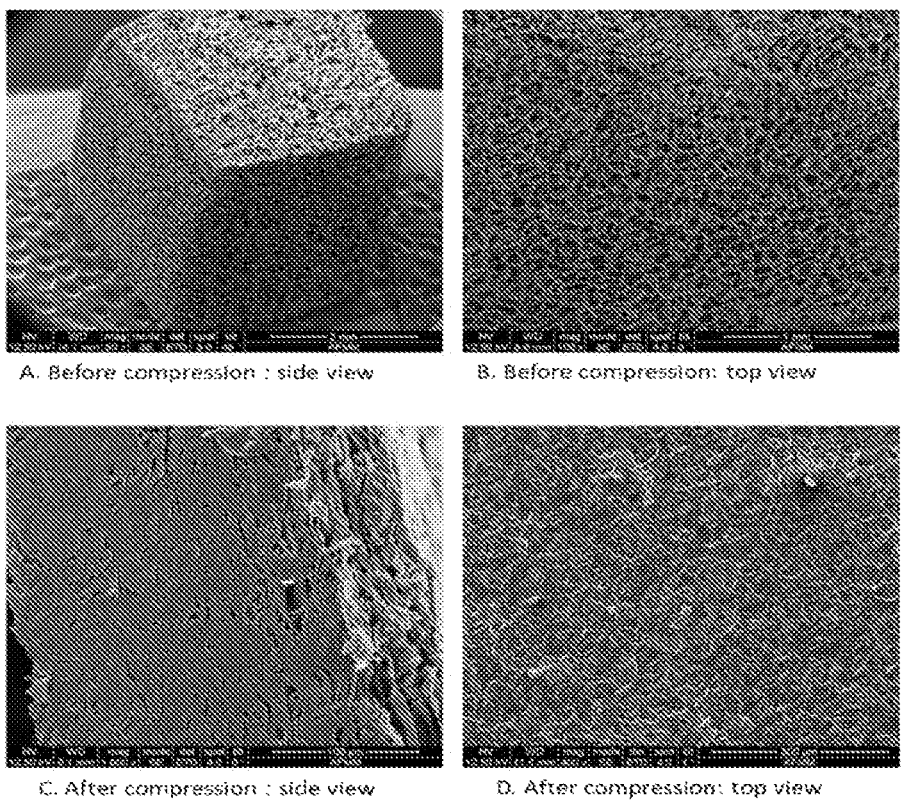

FIG. 7 (A-D) depict the scanning electron microscopic images of drug-loaded chitosan matrix before and after compression.

Figure 8:
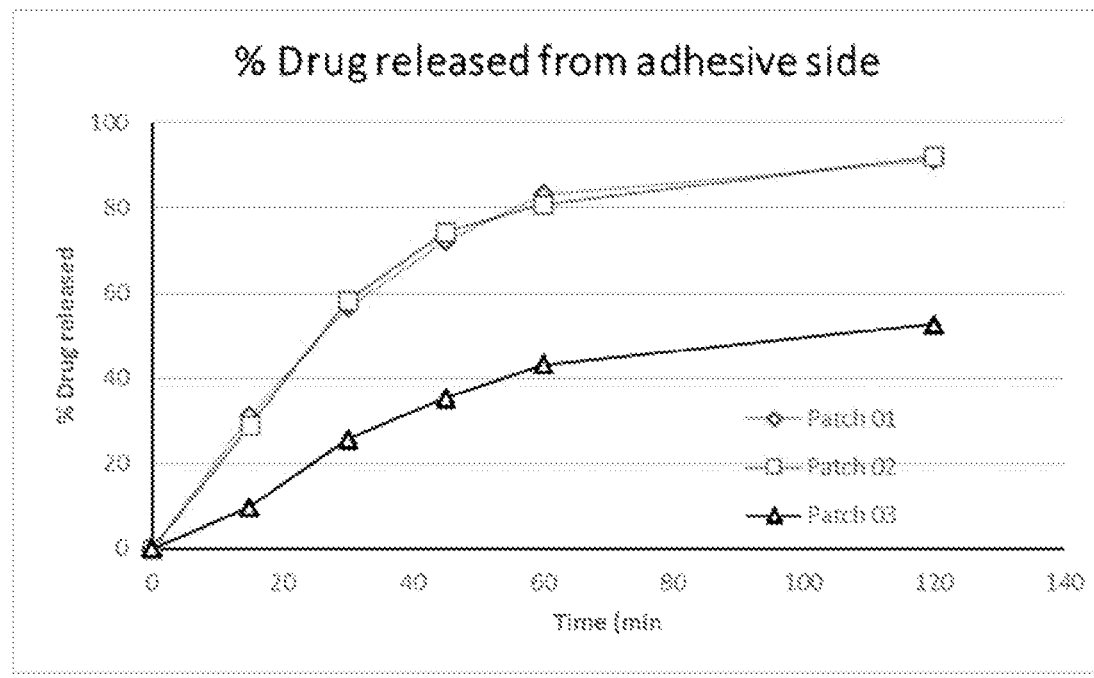

FIG. 8 depicts the results of in vitro drug release of paracetamol from the patches of different configuration; wherein Patch 01 refers to a drug-loaded mucoadhesive patch in single layer; Patch 02 refers to a bilayered patch with water impermeable backing layer over a drug containing mucoadhesive layer; and Patch 03 refers to a tri-layered patch with drug containing layer sandwiched between impermeable backing layer on top and drug-free adhesive layer on bottom.

Figure 9:
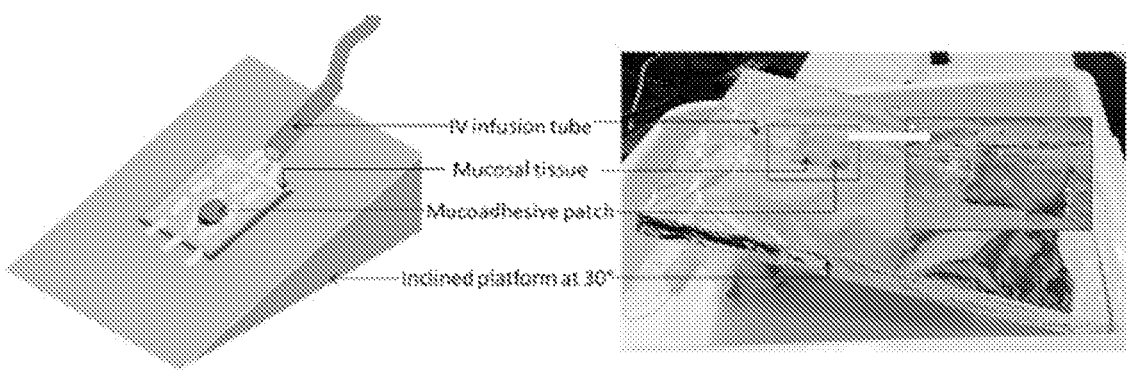

FIG. 9 depicts a prophetic experimental setup for evaluation of ex-vivo residence time. Esophageal mucosa is attached to an inclined platform and artificial saliva is circulated over the mucosa at about 10 mL/min flow rate.

Figure 10:
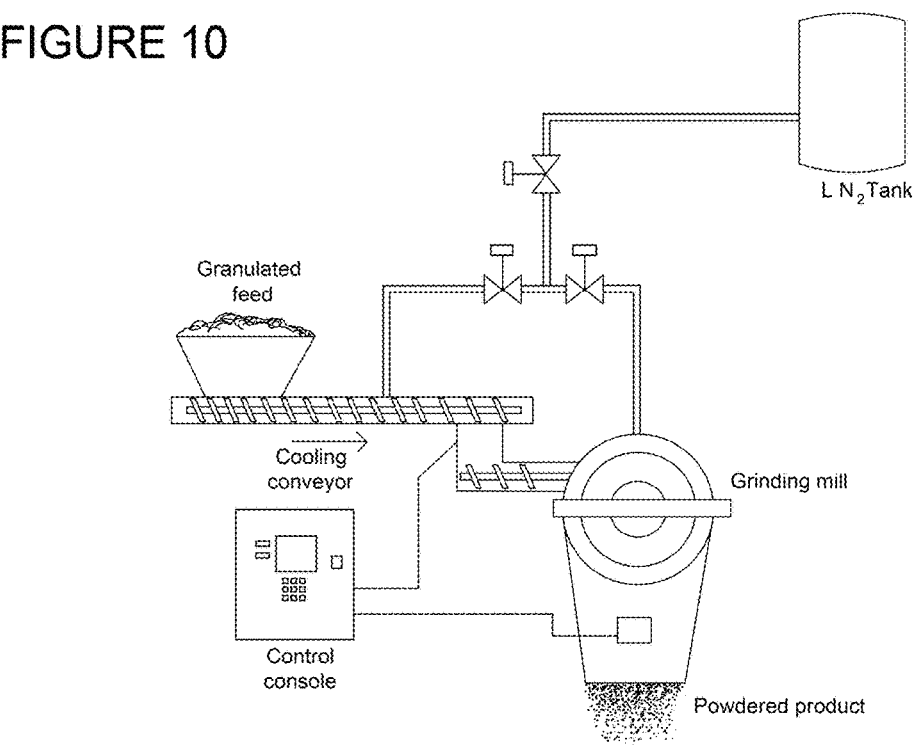
Figure 10:
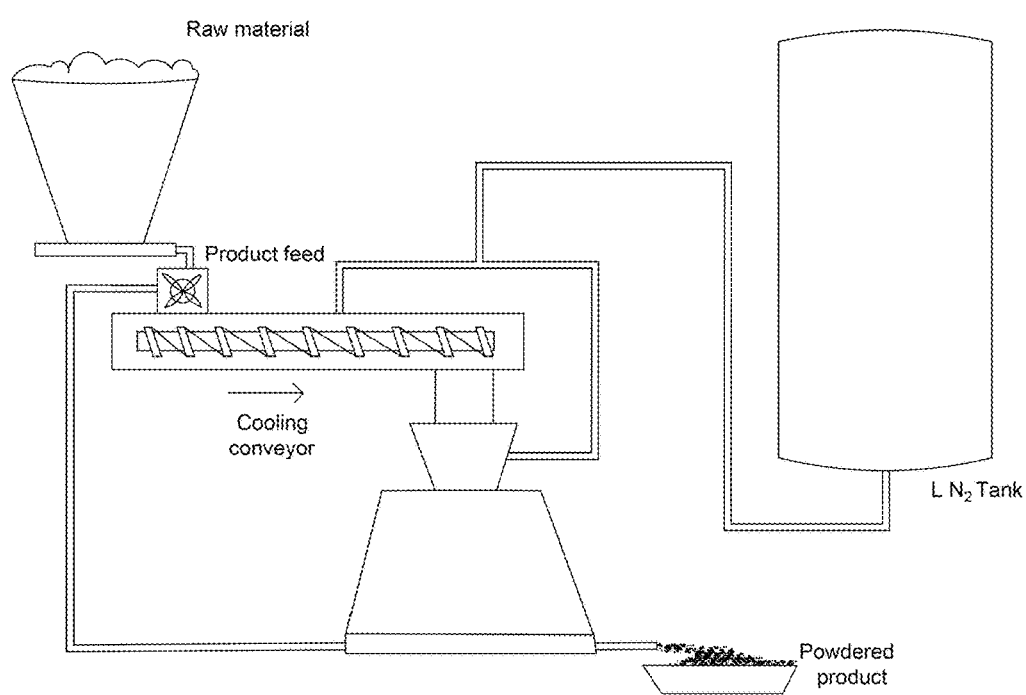

FIG. 10 depicts experimental setup for manufacturing fine powder of porous mucoadhesive matrix of chitosan using a cryogenic grinding mill.

Figure 11:
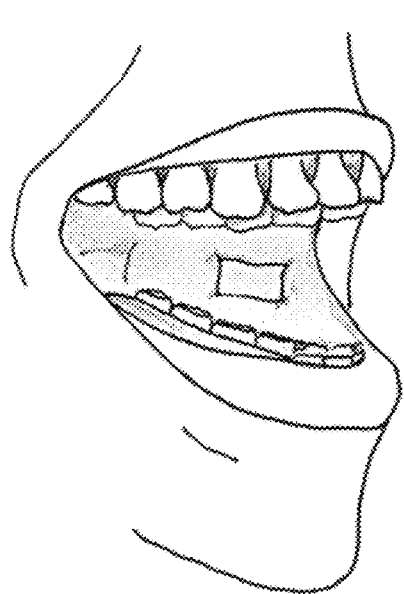
Figure 11:
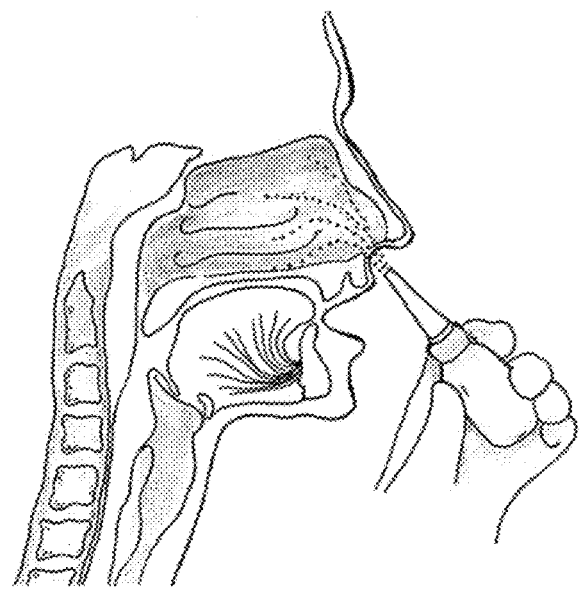
Figure 11:
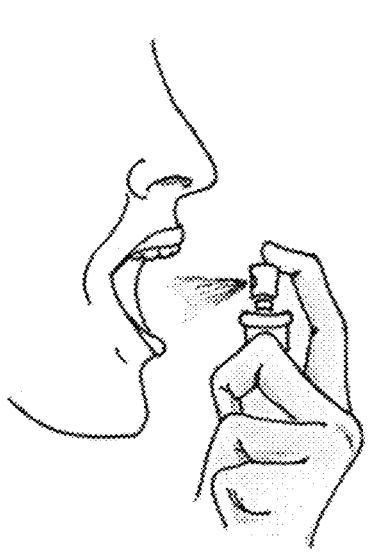
Figure 11:
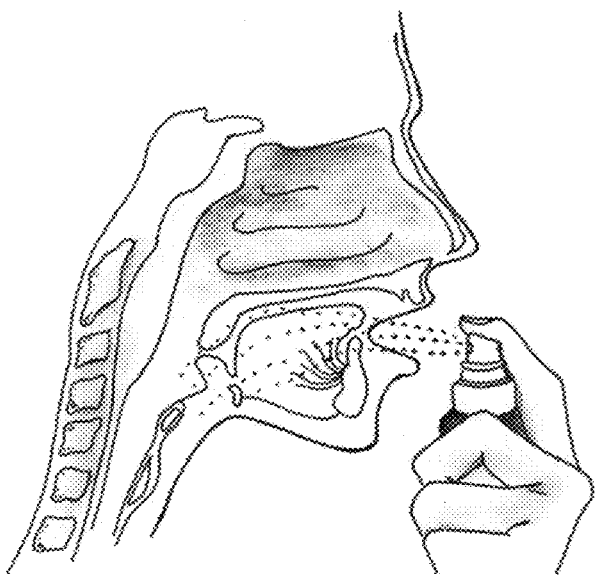

FIG. 11 depicts exemplary methods for application of mucoadhesive patch and mucoadhesive powder formulation to buccal mucosa, nasal administration, oral administration and throat/respiratory administration.

DETAILED DESCRIPTION OF THE DISCLOSURE

To overcome the non-limited drawbacks of the prior art, the present disclosure provides for various preparations, methods and applications thereof.

Particularly, the present disclosure relates to mucoadhesive preparations, methods and applications thereof.

The present disclosure relates to a mucoadhesive preparation comprising chitosan and optionally comprising an organic acid; wherein the mucoadhesive preparation is in a compressed form.

In an embodiment, the organic acid is selected from a group comprising acetic acid, lactic acid, glycolic acid, citric acid and hydrochloric acid; wherein the preparation contains about 50-100% of chitosan and about 0-50% organic acid, preferably 75-85% chitosan and 15-25% of organic acid. and wherein the chitosan is not chemically modified.

In another embodiment, the chitosan in the muchoadhesive preparation is in a form selected from a group comprising, patch, powder, spray, and matrix or a combination thereof.

In yet another embodiment, the mucoadhesive preparation comprises drug.

In still another embodiment, the mucoadhesive preparation is a pre-loaded drug mucoadhesive preparation or a post-loaded drug mucoadhesive preparation.

In still another embodiment, the drug loaded mucoadhesive preparation is multi-layered; and wherein number of layers ranges from 2 to 3.

In still another embodiment, the thickness of the compressed patch ranges from about 10 to 1000 μm.

In still another embodiment, mucoadhesion time of the mucoadhesive preparation ranges from about 4 h to 24 h.

In still another embodiment, the density of the preparation ranges from about 0.05 to 0.5 g/cm$^3$, porosity ranges from about 25 to 95% and pore size ranges from about 10-400 microns.

The present disclosure relates to a method of obtaining a mucoadhesive preparation, comprising acts of:
a) contacting chitosan with organic acid, to obtain a chitosan solution;
b) subjecting the chitosan solution to lyophilisation to obtain dry chitosan sponge; and
c) compressing the dry chitosan sponge to obtain a mucoadhesive preparation.

In an embodiment, mixture of chitosan with organic acid in step a) is stirred to obtain the chitosan solution; and wherein the pH of the mixture is reduced to about pH 2.5 to 5.5 to obtain the chitosan solution in step a).

In another embodiment, the lyophilisation of chitosan solution in step b) involves freezing followed by primary drying and secondary drying; and wherein the compressing is carried out at a temperature ranging from about 0° C. to 30° C.

In yet another embodiment, the freezing is at temperature ranging from about −5° C. to −60° C. for time duration ranging from about 4 to 10 hours; the primary drying is at temperature ranging from about −40° C. to −5° C. for time duration ranging from about 8 to 36 hours in vacuum of about 50 to 250 mTorr; and the secondary drying is carried out at temperatures ranging from about 15° C. to 55° C. for time duration ranging from about 2 to 10 hours.

In still another embodiment, the organic acid is selected from group comprising acetic acid, lactic acid, glycolic acid, citric acid and hydrochloric acid; wherein concentration of the chitosan in step a) is ranging from about 0.5 to 5% and concentration of the organic acid is ranging from about 0.5 to 5%; and wherein the chitosan is not chemically modified.

In still another embodiment, the mucoadhesive preparation is in a form selected from a group comprising, patch, powder, spray, and matrix or a combination thereof.

In still another embodiment, the dry chitosan is compressed into thin patches of thickness ranging from about 10 to 1000 μm using a bench top rolling press or hydraulic press at a temperature lower than 30° C.

In still another embodiment, the chitosan patch can further be prepared into a fine powder having a particle size of about 1-100 μm by grinding the chitosan patch at a temperature ranging from about −200° C. to −5° C.; wherein the grinding is achieved by a technique selected from group comprising planetary ball mill, cryogenic ball mill, and grinding mill.

In still another embodiment, the mucoadhesive preparation comprises one or more drug.

In still another embodiment, drug loading step is carried out prior to lyophilisation to obtain pre-loaded drug mucoadhesive preparation or after lyophilisation to obtain post-loaded drug mucoadhesive preparation; and wherein the drug loading is carried out by contacting the drug with the chitosan solution obtained in step a) or the mucoadhesive preparation obtained in step c).

In still another embodiment, multi-layered mucoadhesive chitosan patch is prepared by acts comprising: compressing a drug-containing chitosan patch with drug-free chitosan patch to obtain diffusion barrier for sustained drug release.

Further, the present disclosure relates to use of a mucoadhesive preparation as drug delivery system.

The present disclosure relates to use of a mucoadhesive preparation in treatment of mucosal disorder.

In an embodiment, the disorder is selected from a group comprising periodontal disease, tooth infections, and gum infections.

The present disclosure relates to a drug delivery system for delivering a drug to a patient in a sustained and controlled manner, the system comprising a mucoadhesive preparation and a drug.

In an embodiment, the drug is administered in a therapeutically effective amount; and the mucoadhesion time of the drug delivery system ranges from about 4 h to 24 h.

The present disclosure relates to a method of delivering one or more drug to a subject in need thereof, wherein the method comprises application of the drug delivery system on mucosal surface of the subject.

In an embodiment, the drug is administered in a therapeutically effective amount; wherein the mucosal surface of the subject is selected from a group comprising buccal, sublingual, pharyngeal, esophageal, gastro-intestinal, nasal, ophthalmic, vaginal and rectal mucosae or any combinations thereof; and wherein the mucoadhesive preparation comprising chitosan and drug remains adhered to the mucosal surfaces for at least 4 to 24 hours.

Mucoadhesion is adhesion between a mucoadhesive material and a mucosal surface. Mucoadhesive preparation refers to a preparation comprising materials which interact with mucus membranes and develop adhesive interactions.

As used herein, the term 'mucoadhesive preparation', 'mucoadhesive chitosan preparation', and 'compressed mucoadhesive preparation' have been used interchangeably to refer to the highly mucoadhesive and compressed chitosan based preparation of the present disclosure which interacts with mucus membranes and develops adhesive interactions. The mucoadhesive preparation of the present disclosure is in a form selected from a group comprising but not limiting to composition, matrix, patch, powder, gel etc. The term 'mucoadhesive preparation' of the present disclosure thus includes 'mucoadhesive patch', 'mucoadhesive powder', 'mucoadhesive gel', etc. The mucoadhesive preparation may be of any shape and size and is porous, flexible, non-erodible and stable.

As used herein, the term 'chitosan matrix' refers to the mucoadhesive preparation of the present disclosure in an uncompressed form.

As used herein, 'mucoadhesive patch', 'mucoadhesive chitosan patch', 'chitosan patch', 'compressed patch' and 'patch' are used interchangeably throughout the present disclosure to refer to the mucoadhesive preparation of the present disclosure in the form of a patch.

As used herein, the term 'mucoadhesive powder' refers to the mucoadhesive preparation of the present disclosure in the form of powder.

As used herein, the term 'mucoadhesive gel' refers to the mucoadhesive preparation of the present disclosure in the form of gel.

As used herein, the term 'residual organic acid' or 'residual acid' refers to the quantity of organic acids in the mucoadhesive preparation of the present disclosure.

As used herein, the term 'room temperature' refers to a temperature range of 22° C. to 27° C.

As used herein, 'drug delivery system', refers to mucoadhesive preparation of the present disclosure for transporting a pharmaceutical compound in the body as needed to safely achieve its desired therapeutic effect. In an embodiment, drug delivery system of the present disclosure comprises compressed chitosan.

As used herein, the term 'drug' and 'pharmaceutical substance', are used interchangeably throughout the present disclosure to refer to a single drug or a combination of drugs.

As used herein, the term 'mucoadhesion time' and 'residence time', are used interchangeably throughout the present disclosure to refer to the time taken by the mucoadhesive preparation to completely disintegrate or detach from the site of application.

Throughout this specification, the word "comprise", or variations such as "comprises" or "comprising" wherever used, will be understood to imply the inclusion of a stated element, integer or step, or group of elements, integers or steps, but not the exclusion of any other element, integer or step, or group of elements, integers or steps.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Any discussion of documents, acts, materials, devices, articles and the like that has been included in this specification is solely for the purpose of providing a context for the disclosure. It is not to be taken as an admission that any or all of these matters form a part of the prior art base or are common general knowledge in the field relevant to the disclosure as it existed anywhere before the priority date of this application.

Chitosan, a cationic polysaccharide, displays cationic charge which has an important role in mucoadhesion through its electrostatic interactions with the anionic mucin chains. In an embodiment of the present disclosure, the chitosan employed has a molecular weight ranging from about 60-1000 kDa, polydispersity index of about 0.8 to 1.2 and the deacetylation degree of more than 50%, preferably about 95%. The chemically modified chitosan comprises any chitosan derivative obtained by covalently bonding other functional groups to the chitosan structure. A few examples of such chemical modifications are: N-trimethylated chitosan, PEGylated chitosan, thiolated chitosan.

In an embodiment, the unmodified chitosan referred in this disclosure comprise the chitosan as well as its salt forms not limited to chitosan-acetate, chitosan-lactate, chitosan-hydrochloride.

The mucoadhesive preparations of the present disclosure comprises chitosan that is not chemically modified, yet retains mucoadhesive characteristics at physiological pH (pH >7.0).

Figure 1:
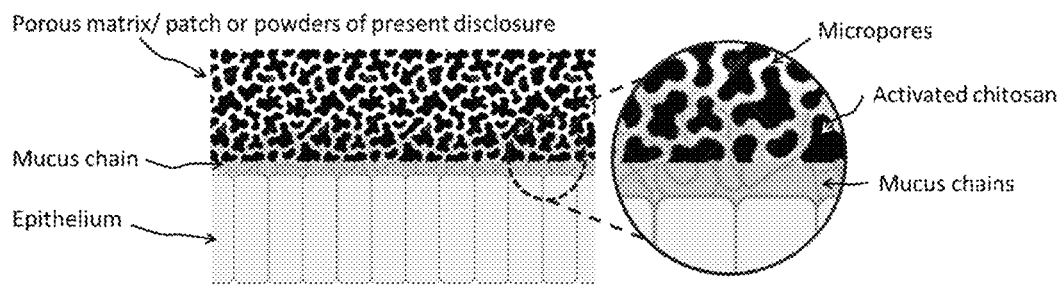

In an embodiment, the mucoadhesive preparation of the present disclosure contains activated (cationic) chitosan molecules within their micropore structures. When the preparation is placed on a mucosal surface, the mucus chains penetrate such micropores and interact with the activated chitosan molecules, resulting in formation of deep interpenetrating network of the mucus within the porous mucoadhesive preparation which ultimately results in higher mucoadhesive force. This mechanism is schematically explained in the FIG. 1.

The mucoadhesive preparation further comprises organic acid.

In an embodiment, the organic acid is selected from a group comprising but not limiting to acetic acid, lactic acid, glycolic acid, citric acid and hydrochloric acid. In an exemplary embodiment, the organic acid is dilute acetic acid.

The chitosan in the mucoadhesive preparation is at a concentration ranging from about 50 to 100% and the organic acid, such as acetic acid, if present, is at a concentration ranging from about 0 to 50%.

In an embodiment, the compressed patch has an acid/residual acid content ranging from about 0-50% of patch weight, preferably about 15 to 25% of patch weight.

In an embodiment of the present disclosure, the mucoadhesive preparation comprising chitosan is formed by subjecting the chitosan solution to lyophilisation and compression. In an embodiment, the compression is carried out at a temperature ranging from about 15 to 25° C. Compression at low temperature helps in avoiding heating up of product and evaporation of the acid during compression, thus ensuring a high acid content in patch for optimum mucoadhesive characteristic of chitosan.

In an embodiment, the compressed mucoadhesive preparation has multiple layers of cationic chitosan. The upper layers slowly release the acid and continuously protonate the chitosan molecules in the bottom layers which are in contact with mucosa. The continuous release of acid prevents complete neutralization of the chitosan molecules in preparations thus provide prolonged mucoadhesion.

In an embodiment of the present disclosure, the mucoadhesive preparation of chitosan may be of any shape and size and is porous and flexible.

In an embodiment, the porous mucoadhesive chitosan preparation of the present disclosure has a density of about 0.05 to 0.5 g/cm$^3$ and porosity of about 25 to 95% with a pore size of about 10-400 microns.

In an embodiment, the thickness of the compressed patch ranges from about 10 μm to 1000 μm.

In an embodiment, the particle size of the mucoadhesive powder ranges from 1 μm to 100 μm.

In an embodiment, the mucoadhesive preparation comprising chitosan does not swell in presence of body fluids (such as saliva, mucus).

In an embodiment of the present disclosure, the mucoadhesive preparation comprising chitosan is highly mucoadhesive, porous and non-erodible.

In another embodiment, the mucoadhesion time of the mucoadhesive preparation ranges from about 4 h to 24 h.

The mucoadhesive preparation of the present disclosure may further comprise one or more drug(s). In an embodiment, the mucoadhesive preparation is a pre-loaded drug-containing mucoadhesive preparation or a post-loaded drug-containing mucoadhesive preparation or a combination thereof.

The present disclosure also relates to a method of obtaining mucoadhesive preparation comprising chitosan, comprising acts of dissolution of chitosan, lyophilisation and compressing, to obtain the mucoadhesive preparation.

In an embodiment, the method of obtaining the mucoadhesive preparation comprises acts of:
a) contacting chitosan with organic acid and optionally stirring, to obtain a chitosan solution;
b) subjecting the chitosan solution to lyophilisation to produce thick, cohesive, dry chitosan/the mucoadhesive chitosan matrix; and
c) compressing the dry chitosan to obtain the mucoadhesive preparation.

In an embodiment, the present disclosure also relates to a method of obtaining mucoadhesive chitosan matrix comprises acts of:
a) contacting chitosan with organic acid, and optionally stirring the mixture, to obtain a chitosan solution; and
b) subjecting the chitosan solution to lyophilization cycle to obtain the mucoadhesive chitosan matrix.

In an embodiment, the mucoadhesive chitosan matrix is further subjected to compression to obtain the mucoadhesive preparation of the present disclosure.

Compression refers to acts of reducing the thickness of lyophilized chitosan matrix by various means such as passing through a roller compression mill or a hydraulic press or manually compressing in two flat surfaces.

In an embodiment, the method of preparing mucoadhesive chitosan matrix comprises acts of dissolution of chitosan and lyophilisation, to obtain the chitosan matrix. In an embodiment, aqueous solution of chitosan is subjected to controlled lyophilization to obtain porous chitosan matrices.

In an embodiment, the dissolution of chitosan involves dissolving chitosan in organic acid. In an embodiment, the pH of the chitosan solution is optionally reduced to about pH 2.5-5.5 to obtain a soluble chitosan solution in step a) of the aforesaid method. In an embodiment, the chitosan is dissolved in dilute organic acid. In an embodiment, the organic acid is selected from group comprising but not limiting to acetic acid, lactic acid, glycolic acid, citric acid and hydrochloric acid.

In an exemplary embodiment, chitosan is dissolved in dilute acetic acid solution.

In an embodiment, the chitosan has molecular weight about 1 kDa to 1000 kDa, preferably about 400 kDa and is at a concentration ranging from about 0.5% w/w to 5% w/w, preferably 2% w/w. In an embodiment, concentration of the organic acid is ranging from about 0.5% w/w to 5% w/w, preferably 0.75% w/w. In an embodiment, the dissolution of chitosan in organic acid is carried out by stirring the chitosan and the acetic acid solution for a time duration ranging from about 2 to 10 hours at a temperature ranging from about 20 to 55° C. to obtain a highly viscous clear solution of chitosan with an average viscosity ranging from about 400 to 800000 cP is obtained. In an embodiment, the chitosan solution obtained is poured into metal trays or plastic moulds of varying sizes and the thickness of resulting porous sponge is controlled by varying the volume of chitosan solution that is poured in the metal trays or moulds.

In an embodiment, the ratio of chitosan and dilute acetic acid solution ranges from about 1:0.15 to about 1:1.

The lyophilisation of chitosan solution in the aforesaid methods involves freezing and drying cycle. In another embodiment, the freezing cycle is followed by drying. In a preferred embodiment, the freezing cycle is followed by primary drying and secondary drying to obtain a porous sheet of dry chitosan/chitosan matrix.

In a preferred embodiment, the lyophilisation of the chitosan solution comprises acts of:
Freezing Cycle: The chitosan solution is snap frozen by exposing to liquid nitrogen or supercooled surface, or the solution is gradually frozen by reducing the solution temperature from about 25° C. to about −60° C., preferably to −30° C. for time duration ranging from about 4 to 10 hours, preferably for 5 hours;

Primary drying: The frozen solution is exposed to a controlled vacuum of about 50 to 250 mTorr, preferably to 70 mTorr, at temperatures ranging from about −40° C. to 15° C. for time duration ranging from about 8 to 36 hours; and Secondary drying: The secondary drying is carried out at temperatures ranging from about 15° C. to 55° C. for time duration ranging from about 2 to 10 hours, preferably 15° C. to 35° C.; or any combinations thereof.

In an embodiment, weight of the frozen chitosan sheets reduces during primary drying by about 90% to 99% due to sublimation of water molecules, preferably by about 93 to 94%. In an embodiment, the secondary drying removes additional moisture from the lyophilized chitosan matrix and gives a final product with a mass of about 3% to 4% of initial weight. In an embodiment, parameters such as density, tensile strength, moisture content, pore size, absorbency, porosity etc. of the chitosan matrix are evaluated.

In an embodiment, the mucoadhesive chitosan matrix is further processed for making chitosan patches or powder.

In an embodiment, the said methods involve lyophilisation of chitosan solution into a porous mucoadhesive chitosan matrix and then processing by compressing into patch or fine powder.

The porous sheet of dry chitosan/the mucoadhesive chitosan matrix is gradually compressed into thin patches. In an embodiment, the mucoadhesive chitosan matrix is gradually compressed into thin patches of thickness ranging from about 10 μm to 1000 μm using a bench top rolling press or hydraulic press. In an embodiment, the porous matrix is gradually compressed by multiple passes through the rolling press, each time reducing the distance between the rollers from an initial of about 10 mm to the desired thickness to achieve a uniformly compressed patch. The chitosan patch can further be prepared into a fine powder having a particle size of about 1-100 μm using an apparatus such as but not limiting to planetary ball mill or a cryogenic ball/grinding mill, or grinding the chitosan sponge at reduced temperature (sub-zero) using dry ice or liquid nitrogen. In an embodiment, the mucoadhesive preparation is in the form selected from a group comprising patch and powder or a combination thereof.

In an embodiment, the pore size of uncompressed matrix is found to be within 50-100 μm range, and the thickness of lamellas forming the porous matrix is around 1-2 μm.

In an embodiment, the pore size of compressed matrix is found to be within 10-20 μm range, and the thickness of lamellas forming the porous matrix is around 1-10 μm.

In an embodiment, the method of the present disclosure is adapted such that the obtained product does not swell in presence of body fluids (like saliva, mucus, etc). The method involves: obtaining the lyophilized sponge of chitosan with high content of residual acid and then compressing it slowly at room temperature (<25 C).

The mucoadhesive chitosan preparation obtained has strong mucoadhesive characteristics even at physiological pH range of about 6.8 to pH 7.4.

In an embodiment, the post-processing maintains the internal porous structure of the chitosan sponge to provide enhanced mucoadhesive characteristics and sustained drug release.

The present disclosure relates to a method of preparing mucoadhesive chitosan patch.

In an embodiment, the method of preparing mucoadhesive chitosan patch comprises acts of:
 a) contacting chitosan with organic acid, and optionally stirring the mixture, to obtain a chitosan solution;
 b) optionally reducing the pH of the solution to about 2.5-5.5 to obtain a soluble chitosan solution;
 c) subjecting the chitosan solution to a pre-determined lyophilisation cycle to produce thick, cohesive, porous sheet of dry chitosan; and
 d) compressing the sheet of chitosan to obtain the chitosan patch.

In an embodiment, the organic acid is dilute acetic acid present at a concentration ranging from about 0.5% w/w to 5 w/w and chitosan is at a concentration ranging from about 0.5% w/w to 5% w/w; and wherein the active pharmaceutical agent/drug is selected from a group comprising any water soluble, water insoluble drugs and thermally labile drug for local or systemic effect.

In a non-limiting embodiment, the drug is selected from a group comprising psychiatric drug such as asenapine; opioid drugs such as buprenorphine, naloxone, fentanyl; cardiovascular drug such as nitroglycerin; nausea medication such as Prochlorperazine; hormone replacement therapy such as testosterone, nicotine as a smoking cessation aid; and chlorhexidine for periodontal diseases.

In an embodiment, the present disclosure also relates to a method of obtaining drug-loaded mucoadhesive chitosan preparation. In an embodiment of the present disclosure, the method of obtaining the drug-loaded mucoadhesive chitosan preparation such as patch comprises acts of preparing a highly viscous chitosan solution, lyophilisation and compression.

In an embodiment, active pharmaceutical agent/drug/ingredient is loaded in the mucoadhesive preparation by mechanisms such as pre-loading and post-loading or any combination thereof. In an embodiment, pre-loading of the drug comprises act of dissolving active pharmaceutical agent in the chitosan solution prior to lyophilisation. In another embodiment, the active agent is incorporated in the lyophilized chitosan matrix/patch by post-loading method by incubating the lyophilized chitosan matrix/patch in a solution containing the active agent to achieve sufficient drug loading in the porous structure of the chitosan matrix/patch. In an embodiment, the terms 'active pharmaceutical agent', 'active agent', 'agent', 'drug', 'ingredient', 'pharmaceutical substance' are interchangeably used.

In an exemplary embodiment, the method of obtaining pre-loaded drug-loaded mucoadhesive chitosan patch comprises acts of:
 a) contacting chitosan with organic acid, and optionally stirring the mixture, to obtain a chitosan solution;
 b) optionally reducing the pH of the solution to about 2.5-5.5 to obtain a soluble chitosan solution;
 c) optionally dissolving active pharmaceutical agent/drug in the chitosan solution;
 d) subjecting the chitosan solution to a pre-determined lyophilization cycle to produce thick sheet of dry chitosan; and
 e) compressing the sheet of chitosan to obtain the chitosan patch.

In an embodiment, the preparations provide high drug loading by entrapping the drug/active molecules in microporous structure of chitosan sponges. The drug is then immobilized in micropores by compression of lyophilized-chitosan sponges, which gives sustained drug release. The method allows loading of drugs with different physicochemical properties (solubility, stability etc). Both water soluble and insoluble drugs can be loaded and released in a sustained manner from these patches. Even, thermally labile drugs can be loaded.

In an embodiment, the thick sheet of dry chitosan is drug-loaded porous matrices of chitosan and is processed by gradually compressing the matrix to a thin patch, using a bench top rolling press or hydraulic press to achieve a uniformly compressed unidirectional drug-loaded patch.

In an exemplary embodiment, the method of obtaining post-loaded drug-loaded mucoadhesive chitosan patch comprises acts of:
a) contacting chitosan with organic acid, and optionally stirring the mixture, to obtain a chitosan solution;
b) optionally reducing the pH of the solution to about 2.5-5.5 to obtain a soluble chitosan solution;
c) subjecting the chitosan solution to a pre-determined lyophilization cycle to produce thick sheet of dry chitosan;
d) incubating the chitosan matrix in a solution containing the active agent/drug to achieve sufficient drug loading in the porous structure of the chitosan patch.
e) compressing the drug-containing chitosan matrix to obtain the drug-containing chitosan patch.

In an embodiment, method of post-loading drug-loaded mucoadhesive chitosan patches involve treating the drug-free porous matrix of chitosan with a solution of desired drug(s). This method is suitable for compounds which are insoluble or unstable in the acidic chitosan solution.

In an embodiment, the chitosan solution is highly viscous and lyophilizable. In an embodiment, the organic acid is selected from group comprising but not limiting to acetic acid, lactic acid, glycolic acid, citric acid and hydrochloric acid or a combination thereof.

In another embodiment, the sheet of chitosan is processed to obtain the patch by passing the thick porous sheet of chitosan through multiple cycles of compression. In yet another embodiment, the porous matrix is gradually compressed by multiple passes to obtain uniformly compressed patch. In an embodiment, the compression is carried out by using an instrument selected from a group comprising but not limiting to hydraulic press, rolling mill, bench top roller, etc. In an exemplary embodiment, the distance between the rollers is reduced each time, from an initial of about 10 mm to the desired thickness of about 10 to 1000 μm. In an embodiment, the thickness of the thin patch obtained is ranging from about 0.1 to 1 mm, preferably from about 100 to 300 μm. In an embodiment, pore size of the porous chitosan patch optionally loaded with drug is ranging from about 10 to 400 μm, preferably about 50 to 100 μm. Further, each lamella of activated chitosan which forms the individual cells of porous matrix has a thickness ranging from about 1 to 10 μm.

In an embodiment, the chitosan patch/sponges is cut into pieces of about 1 cm² discs and soaked in ethanolic solution of the drug for 30 to 120 min; wherein the concentration of the drug ranges from about 1% to 5% w/v. The drug-loaded sponges are then taken out and air dried at room temperature of about 25° C. till all ethanol is evaporated. The drug-loaded sponges are then compressed to obtain the post-loaded drug patches; wherein the drug is selected from a group comprising water soluble, insoluble drugs and thermally labile drugs. The method is optimized for the initial drug concentration and incubation time to achieve optimum drug-loading efficiency. The drug-loading efficiency is estimated by extracting the drug from the patches and quantifying it using a UV-spectrophotometer.

In a non-limiting embodiment, the drug is selected from a group comprising psychiatric drug such as asenapine; opioid drugs such as buprenorphine, naloxone, fentanyl; cardiovascular drug such as nitroglycerin; nausea medication such as Prochlorperazine; hormone replacement therapy such as testosterone, nicotine as a smoking cessation aid; and chlorhexidine for periodontal diseases.

In an embodiment of the present disclosure, the drug-loaded mucoadhesive patch has a configuration selected from a group comprising: Patch 01 wherein the drug-loaded mucoadhesive patch is in a single layer (011); Patch 02 which contains a water impermeable backing layer (022) over a drug containing mucoadhesive layer (021); or Patch 03 which contains a drug containing layer (031) sandwiched between impermeable backing layer (032) on top and drug-free adhesive layer (033) at bottom (FIG. 6).

In an embodiment of the present disclosure, the drug-loaded mucoadhesive patch provides for unidirectional or bidirectional or multidirectional drug release.

In an embodiment, the drug release property of the patch is evaluated in a physiological buffer having pH ranging from about 6.8 to 7.4 to simulate conditions in oral cavity.

In a non-limiting embodiment of the present disclosure, the Patch 03 (FIG. 6) provides for slow release from the adhesive side, indicating its suitability for sustained drug delivery. The slower release occurs since the drug-free adhesive layer (33) serves as a diffusion barrier for burst release from the patch.

In an embodiment, unidirectional drug release properties of the drug-loaded patches are evaluated in a Krebs Ringer buffer (KRB) at about pH 6.8 to simulate conditions in oral cavity, wherein the patches are held in horizontal diffusion cell with backing layer facing the donor compartment. The donor and receiver compartments are filled with the release media Krebs Ringer buffer pH 6.8 and samples are withdrawn from the receiver compartment at predetermined time intervals. At the end of the study all samples are analyzed using UV spectrophotometer. The results obtained show slow release of the drug in the receiver compartment, indicating its suitability for sustained drug delivery.

In an embodiment, the internal structure of post-loaded drug-containing patches before and after compression is examined using scanning electron microscopy (FIG. 7). The pore size of the drug-containing matrix is slightly smaller than the drug-free matrix. After compression, the porous matrix has a closed pore structure, wherein the multiple lamellas are stacked, but do not fuse together. This unique arrangement of the lamellas allows for the enhanced mucoadhesion and sustained drug release even in the patches prepared using post-loading method.

In an embodiment, the invitro drug release is evaluated in Krebs Ringer buffer. The results indicate that the drug release kinetics can be controlled by varying the initial drug content of the patches.

In an embodiment, the drug release ranges from about 2 to 24 hours.

In an embodiment, a burst drug release is observed for first 2 hours, followed by a sustained drug release for up to 24 hours.

In an embodiment, the drug release is further modified by preparing multi-layered mucoadhesive chitosan patches.

In another embodiment of the present disclosure, method of obtaining a multi-layered drug loaded mucoadhesive patch for unidirectional drug release, comprises acts of:
a) freezing a layer of drug-free chitosan layer at about −60 to −20° C. for about 2 to 10 hours in metal trays or moulds;
b) pouring a layer of drug-containing chitosan solution over frozen drug-free chitosan solution;
c) lyophilizing the layers obtained in steps a) and b) followed by gradual compression at temperature ranging from about 20 to 50° C. by passing through a rolling mill to obtain a patch with about 0.1 to 1 mm thickness; and d) coating the drug-reservoir side of the patch with a water impermeable polymer to obtain the multilayered drug loaded patch.

In an embodiment, the water impermeable polymer is selected from group comprising ethyl cellulose, methyl cellulose, hydroxyethyl cellulose, Polyvinyl acetate phthalate and Methacrylic acid copolymers.

In an exemplary embodiment, the unidirectional drug release property of the patch is evaluated in a Krebs Ringer Bicarbonate buffer having pH ranging from about 6.8 to 7.4, to simulate conditions in case of oral cavity.

In another embodiment of the present disclosure, the method of obtaining a multi-layered drug-loaded mucoadhesive patch comprises acts of:
 a) dissolving drug in the chitosan solution followed by lyophilization to obtain a drug containing mucoadhesive reservoir;
 b) compressing the drug-containing chitosan matrix with a drug-free chitosan matrix on one side to serve as a diffusion barrier.
 c) Coating the top-side of drug-containing patch with an impermeable polymer film to obtain the multi-layered drug loaded mucoadhesive patch.

In an embodiment, the impermeable polymer film is selected from group comprising but not limiting to ethyl cellulose, methyl cellulose, hydroxyethyl cellulose, Polyvinyl acetate phthalate and Methacrylic acid copolymers. In an embodiment, the aforesaid method provides for sandwiching the drug-containing layer between the backing layer and drug-free patch.

In an exemplary embodiment, a water-soluble model drug such as paracetamol at a concentration ranging from about 0.5 to 2% w/w is dissolved in dilute acetic acid taken at a concentration of about 0.25 to 3% w/w solution along with about 0.5 to 5 w/w of chitosan.

In another exemplary embodiment, the solution comprising paracetamol, chitosan and acetic acid is used to prepare the paracetamol-loaded porous matrices of chitosan. The paracetamol-loaded porous matrix is compressed to a thin patch of about 0.1 to 1 mm thickness. The pore size of the drug-loaded porous matrix obtained ranges from about 10 to 400 µm, preferably about 50 to 100 µm. In an embodiment, the patch is obtained by passing the thick sheets of drug-loaded porous chitosan matrix through multiple cycles of compression through a hydraulic press or rolling mill. In a preferred embodiment, the thickness of obtained patch is in the range of about 0.1 to 1 mm, preferably about 0.1-0.3 mm.

In an embodiment of the present disclosure, in vitro mucoadhesion and residence time study is performed to evaluate the performance of a mucoadhesive drug delivery system intended to remain at the absorption site for prolonged duration and residence time.

In a preferred embodiment, method for measuring ex vivo residence time comprises acts of:
 a) The esophageal mucosa is separated from the adhering connective tissue and dissected into about 50×50 mm sized pieces.
 b) The dissected mucosa is fixed on an inclined support platform (about 30° angle) with apical surface facing upward.
 c) The mucosa is continuously hydrated with the artificial saliva (about 0.5% mucin in PBS pH 7.0), at a rate of about 10 mL/min using an infusion set to mimic the physiological flow of mucus/saliva secretions over the applied patch.
 d) The samples are applied on the tissue by gently pressing the patches on to the mucosal surface with index finger for a time duration of about 30 sec.
 e) The residence time is determined by recording the duration of displacement from the adhesion site.

In an embodiment, the patches of the present disclosure exhibit at least about 4 hours of adhesion to the mucosa.

In an embodiment, the patches of the present disclosure exhibit at least about 24 hours of adhesion to the mucosa.

In a non-limiting embodiment, the present disclosure relates to a compressed mucoadhesive chitosan patch and a method of preparing the same. In an embodiment, the compressed patches maintain the mucoadhesive interactions for very long periods in comparison to the uncompressed matrix of chitosan. The mechanism for the improved mucoadhesive properties is the pH microenvironment within the compressed porous structure of the matrix. The compression process creates mini reservoirs of highly cationic chitosan chains containing high concentration of the acid within the porous structure which provides a significant surface area for the adsorption of mucus, but does not swell immediately as the cationic chitosan chains are slowly exposed to the mucus. The overall effect is very slow neutralization of the chitosan chains, which results in prolonged mucoadhesive force and mucoadhesion to the biological tissue.

In an embodiment, the present disclosure also relates to method of obtaining fine powder of porous chitosan matrix and patches thereof.

In an embodiment, the powder is obtained using an instrument/technique selected from a group comprising but not limiting to planetary ball mill, cryo-mill (cryogenic ball mill), and grinding the chitosan sponge at reduced temperature (sub-zero) using dry ice or liquid nitrogen. Conventional milling methods do not work on chitosan sponge as they are soft and non-brittle at room temperature. The grinders can cause increase in temperature which can severely affect the mucoadhesive characteristics of chitosan matrices. The method of obtaining the powder as per the present disclosure maintains the ideal mucoadhesive characteristics of the lyophilized sponge/matrix/preparation. In an embodiment, the chitosan matrix powder has a particle size ranging from about 1-100 µm, preferably about 10-50 µm.

In an embodiment, size reduction at reduced temperature is necessary to prevent the complete evaporation of acetic acid and neutralization of cationic chitosan chains which directly affects its mucoadhesive characteristics.

In an embodiment, the cryogenic milling comprises following steps:
 i. cutting the compressed chitosan matrix or patches into coarse particles of about 1 to 10 mm size using an instrument such as but not limiting to blade or cutter,
 ii. placing the coarse particles of said matrix or patches in a ball mill attritor with grinding media,
 iii. maintaining temperature of the attritor at about −150 to −50° C. using liquid nitrogen,
 iv. activating the attritor, whereby the coarse powder is repeatedly impinged between grinding media within the attritor,
 v. deactivating the attritor and removing the cryo-milled mucoadhesive powder from the attritor;
 vi. optionally continuing the method until particle size of about 10-100 microns is achieved; and vii. optionally separating the mucoadhesive powder from the grinding media by sieving out the grinding media; or any combinations thereof.

In a non-limiting embodiment, the grinding media comprises components selected from group comprising metal ball or dry ice.

In an embodiment, the grinding media comprises balls of varying diameters of about 10 to 100 mm of materials selected from a group comprising but not limiting to stainless steel, teflon, etc.

In an embodiment, the grinding media for milling process comprises dry ice (frozen carbon dioxide) pellets. This allows for obtaining the final mucoadhesive powder without the final sieving step as the dry ice evaporates at room temperature. The dry-ice pellets avoid contamination of the powder by components of the grinding media.

In an embodiment, formulating the mucoadhesive preparation into powder has added advantage of being administered as a dry mist using a spray device.

In an embodiment, the chitosan matrix powder is applied to the mucosal surfaces such as but not limiting to oral, nasal mucosae, ocular, vaginal or rectal cavities.

The present disclosure relates to use of mucoadhesive preparation comprising chitosan and drug as therapeutic delivery system.

In an embodiment, the mucoadhesion time of the mucoadhesive preparation ranges from about 4 h to 24 h.

The present disclosure relates to a drug delivery system for delivering therapeutic amounts of a pharmaceutical substance to a patient in a sustained and controlled manner, the system comprising a mucoadhesive preparation comprising chitosan and a pharmaceutical substance/drug.

In an embodiment, the drug is present in a therapeutically/prophylactic effective amount.

In an embodiment, the concentration of drug in the preparation ranges from about 1-20%, preferably 5 to 20% w/w.

In an embodiment, the mucoadhesion time of the drug delivery system ranges from about 4 h to 24 h.

In an embodiment, the present disclosure provides for mucosal delivery of therapeutic agents through mucoadhesive preparation.

In an embodiment, the present disclosure also relates to use of the mucoadhesive preparation (such as but not limiting to patch, matrix, powder) as therapeutic drug delivery systems.

In an embodiment, the present disclosure relates to application of the muchoadhesive chitosan preparation (such as but not limiting to patch, matrix and powder) in a subject for managing a condition.

In an embodiment, the condition is any disease/disorders/infection of mucosal surfaces. In an exemplary non-limiting embodiment, the condition is selected from a group comprising but not limiting to periodontal diseases, tooth or gum infections, or any combinations thereof.

In an embodiment, the present disclosure relates to use of the mucoadhesive preparation (such as but not limiting to patch, matrix, powder) for the treatment of mucosal disorders.

In an embodiment, the application of the mucoadhesive powder preparation is done manually or by device such as but not limiting to a spray device or a simple powder dispenser.

The present disclosure also relates to a method of delivering therapeutic amounts of a pharmaceutical substance to a subject in need thereof, wherein the method comprises application of mucoadhesive preparation comprising chitosan and drug, on mucosal surface of the subject.

In an embodiment, the concentration of drug in the preparation ranges from about 1-20%, preferably 5 to 20% w/w; and wherein the mucosal surface of the subject is selected from a non-limiting group comprising oral, nasal mucosae, throat, ocular, vaginal, or rectal cavities (FIG. 11).

In an embodiment, the mucoadhesive preparation comprising chitosan and drug remains adhered to the mucosal surfaces for at least 4 to 24 hours.

In yet another embodiment of the present disclosure, the subject is a mammal, including human beings.

In another embodiment, the mucoadhesive patch and powder are intended for the local or systemic administration of a single or multiple pharmaceutical agent and may be applied to any mucosal surfaces selected from a group comprising buccal, sublingual, pharyngeal, esophageal, gastro-intestinal, nasal, ophthalmic, and vaginal mucosae or any combinations thereof.

In an embodiment of the present disclosure, the mucoadhesive preparation is used to treat periodontal disease, tooth and/or gum infections, due to the anti-bacterial property of the chitosan.

In an embodiment, the mucoadhesive patch and mucoadhesive powder formulation are applied as buccal patch to buccal mucosa, nasal administration, oral administration and throat/respiratory administration as shown in FIG. 11.

In an embodiment of the present disclosure, the mucosal routes of administration of mucoadhesive offer higher systemic bioavailability for some drugs by circumventing the gastrointestinal tract and the hepatic first pass effect.

In an embodiment of the present disclosure, the mucoadhesive dosage preparations/forms/systems are ideal for sustained delivery. They bind to the mucosal surfaces and provide an intense and prolonged attachment to the absorption site. This allows formulations to immobilize the drug at the target site and maintain its therapeutic concentrations for a prolonged duration.

In another embodiment of the present disclosure, the term 'managing' or 'management' includes preventing, treating and healing of a disease condition or disorder or ill effects or side effects. The term also encompasses maintenance of the optimum state and prevention of the further progress in the disease condition or disorder or ill effects or side effects.

In an embodiment, the foregoing descriptive matter is illustrative of the disclosure and not a limitation. Providing working examples for all possible combinations of optional elements in the composition and process parameters is considered redundant. Descriptions of well-known/conventional methods and techniques are omitted so as to not unnecessarily obscure the embodiments herein.

While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein.

Further, the invention herein provides for examples illustrating the above described embodiments, and in order to illustrate the embodiments of the present invention, certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1: Preparation and Evaluation of Lyophilized Chitosan Matrix 1.1 Preparation of lyophilized chitosan matrix Porous chitosan matrices were obtained by controlled lyophilization of an aqueous solution of chitosan. Chitosan with an average molecular weight of about 400 kDa was dissolved in dilute acetic acid solution. The concentration of the chitosan was maintained at about 2% w/w; whereas, the concentration of acetic acid solution was kept at about 0.75% w/w. The dissolution of chitosan required between about 8 hours of stirring at a temperature of about 25° C. The above process resulted in a highly viscous clear solution of chitosan with an average viscosity of about 40000 cP. Nevertheless, chitosans with different molecular weights, and varying chitosan and acetic acid concentrations can be employed to obtain chitosan solutions with viscosities ranging from 400 to 800000 cP (Table 1).

TABLE 1

Viscosities of chitosan solutions obtained using different combinations of chitosan and acetic acid concentrations

| Chitosan concentration (w/w) | Acetic acid concentration (w/w) | Viscosity (cP) | Dissolution duration (h) |
|---|---|---|---|
| 0.5% | 0.5% | 421 | 4 to 8 |
| 1% | 0.75% | 3219 | 3 to 6 |
|  | 1.0% | 2500 | 2 to 3 |
| 2% | 0.75% | 42190 | 5 to 10 |
|  | 1.0% | 38621 | 4 to 9 |
|  | 2.0% | 36623 | 4 to 8 |
| 5% | 0.75% | NA | NA |
|  | 2.0% | >100000 | 15-24 |
|  | 5.0% | 800000 | 12-24 |

Table 1 shows the viscosities of chitosan solutions obtained by employing different combinations of chitosan and acetic acid concentrations confirm the achievement of desired properties of chitosan solutions.

The chitosan solution was poured into metal trays or plastic moulds of varying sizes of about 1000 cm². The thickness of resulting porous sponge was controlled by varying the volume of chitosan solution that was poured in the metal trays or molds. The chitosan solution was subjected to different lyophilization processes as shown in FIGS. 2 (*a*), (*b*) and (*c*) to obtain chitosan matrix.

The lyophilization process was carried out according to the following steps, the specific details of each cycle are shown in FIGS. 2 (*a*) to 2 (*c*):
 a) Freezing Cycle: The chitosan solution was frozen by reducing its temperature from about 25° C. to −30° C. for about 4 to 10 hours.
 b) Primary drying: The frozen solution was exposed to a controlled vacuum of about 50 to 250 mTorr at temperatures ranging from about −40° C. to 15° C. for about 8 to 36 hours. During this step the weight of frozen sheets reduced by about 93% to 94% due to sublimation of water molecules.
 c) Secondary drying: The secondary drying was carried out at temperatures ranging from about 15° C. to 35° C. for about 2 to 10 hours. This final step removed the additional moisture from the lyophilized matrix and gave a final product with a mass of about 3% to 4% of initial weight.

1.2 Evaluation of Lyophilized Chitosan Matrices

The obtained lyophilized chitosan matrices were evaluated for their tensile strength, residual acid content, pore size, absorbency and processed for making patches or powder. Table 2 shows the important characteristics of the obtained patches using different lyophilization cycles detailed in FIG. 2.

Figure 3A:
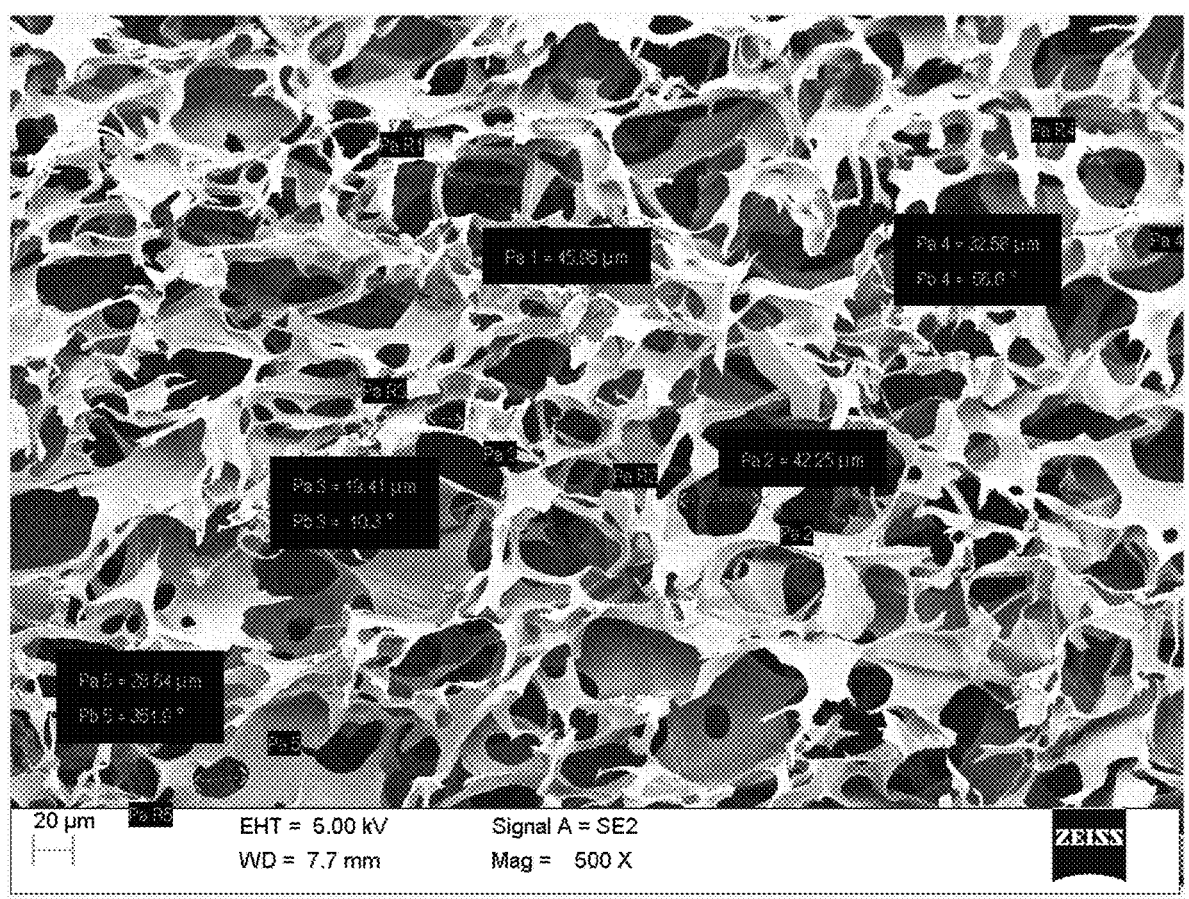
Figure 3B:
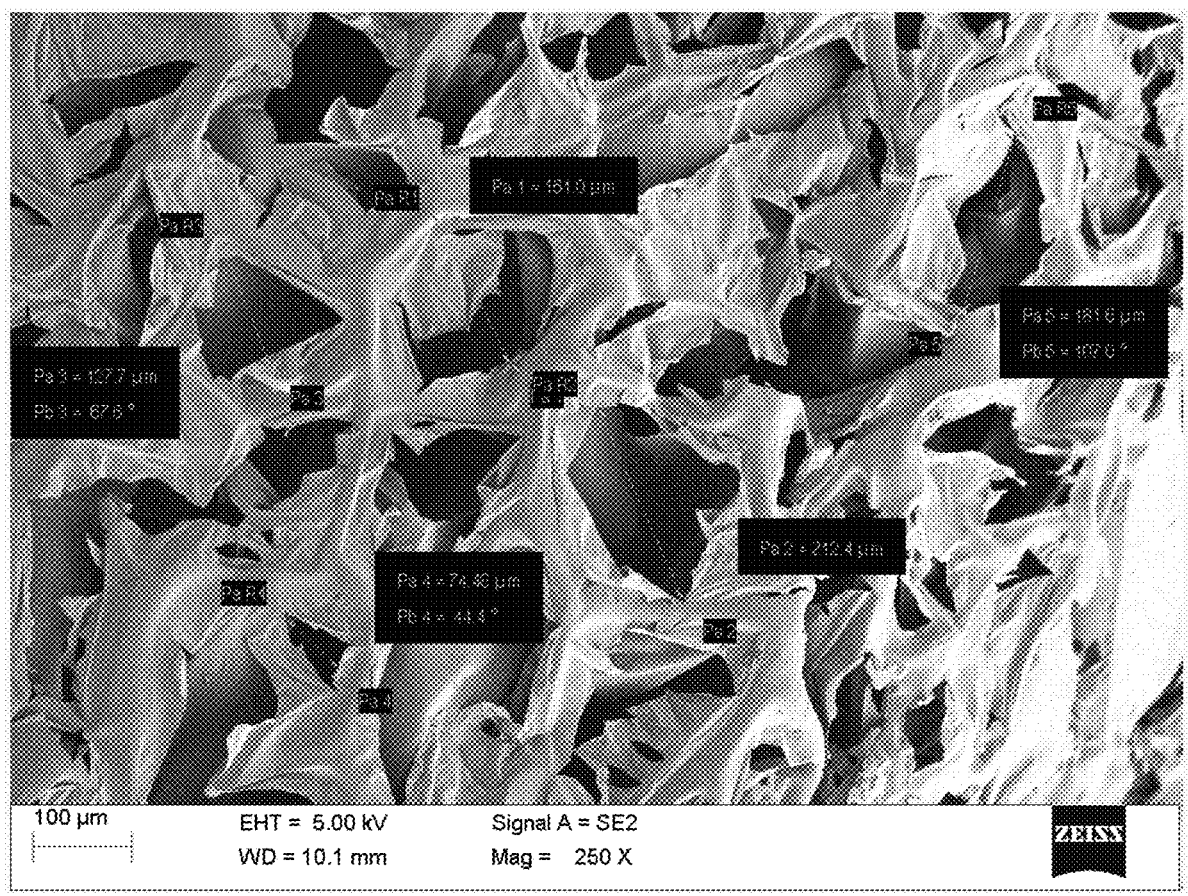

The representative scanning electron microscopic images showing porous structure of lyophilized matrices before compression are shown in FIGS. 3 (*a*) and (*b*). The pore size of uncompressed matrix was found to be within 50-200 μm range, additionally the thickness of lamellas forming the porous matrix was around 1-2 μm. The duration of lyophilization process appeared to affect the pore size as well as the residual acid content in lyophilized matrices.

TABLE 2

Characteristics of lyophilized chitosan matrices

Figure 2A:
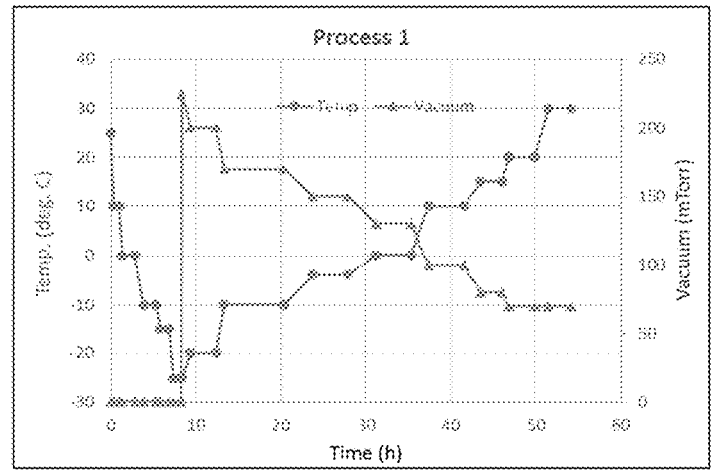
Figure 2B:
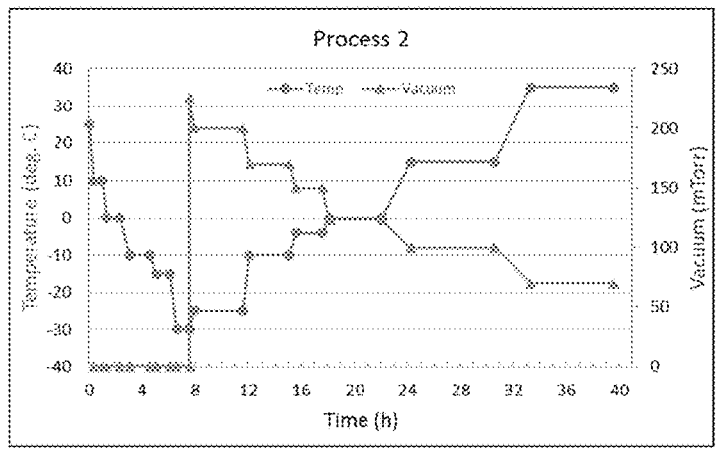
Figure 2C:
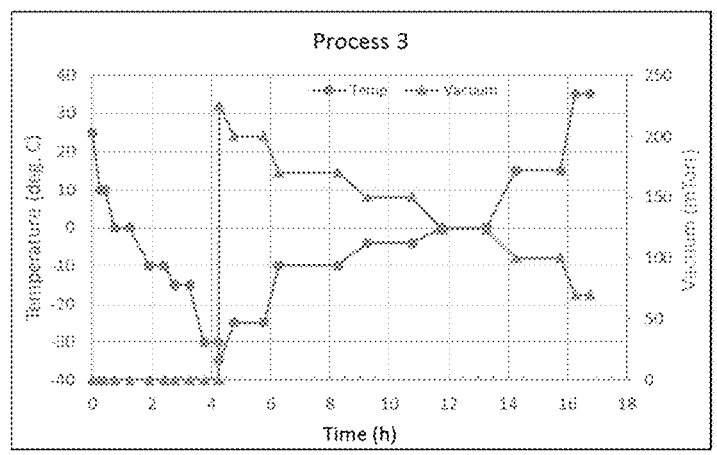

| Lyo Process details | Acid content (% w/w) | Tensile strength (N/mm²) | Avg Pore size (μm) | Absorbency (X times dry wt) |
|---|---|---|---|---|
| FIG. 2a | 19.5 ± 6.3% | 37.4 ± 2.1 | 110 ± 53 | >40 x |
| FIG. 2b | 24.9 ± 5.8% | 33.7 ± 1.9 | 155 ± 79 | >40 x |
| FIG. 2c | 29.3 ± 4.6% | 35.2 ± 2.5 | 198 ± 120 | >40 x |

Table 2 shows the characteristics such as acid content, tensile strength, average pore size and absorbency employed in the present lyophilized chitosan matrices confirm the achievement of desired properties of lyophilized chitosan matrices.

Example 2: Preparation of Mucoadhesive Patch

Figure 4:
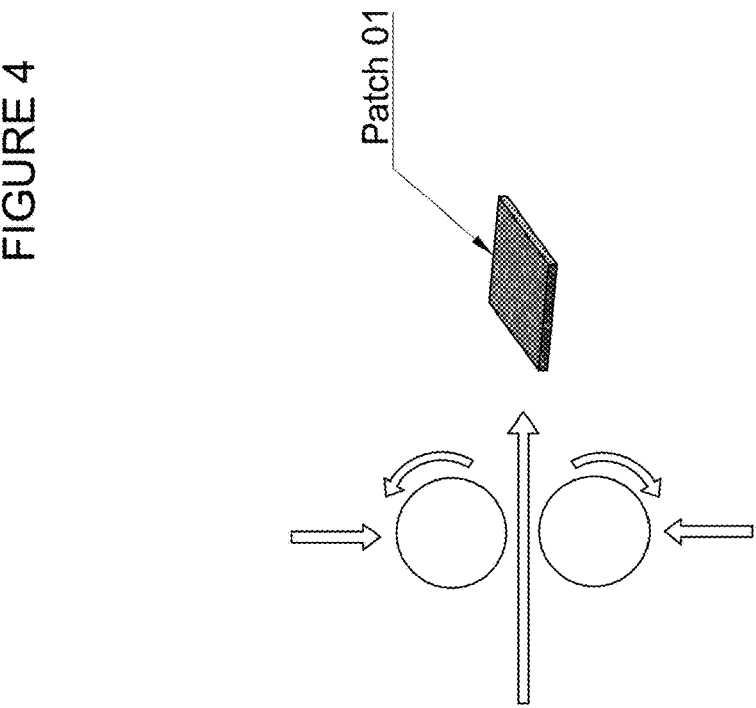
FIG. 4 depicts the process of compressing thick porous matrix into a thin compressed patch using a rolling press.
Figure 4:
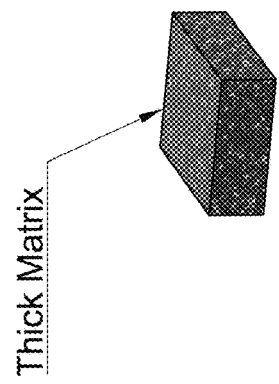
Figure 4:
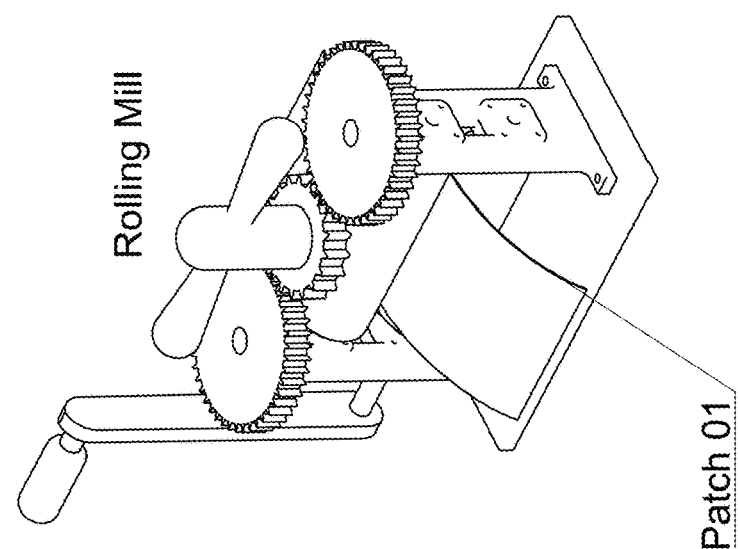
Figure 5:
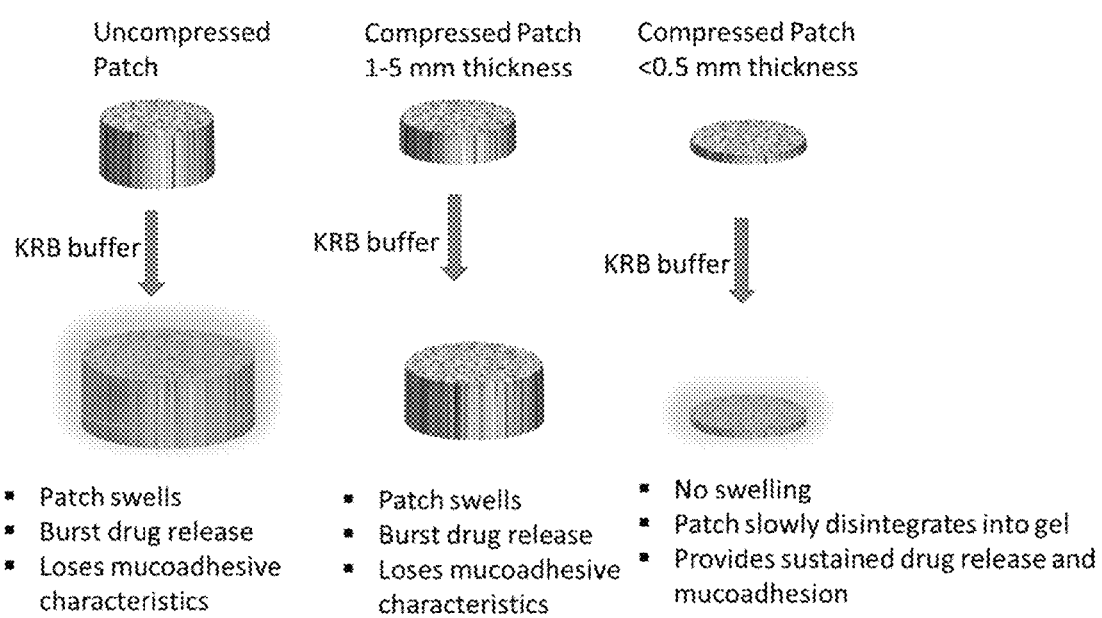
FIG. 5 depicts the effect of compression on swelling behaviour and drug release from mucoadhesive patches.

Porous lyophilized matrix obtained in the above example was compressed into thin patches of thickness ranging from about 10 to 1000 μm using a bench top rolling press or hydraulic press, as shown in FIG. 4. To achieve a uniformly compressed patch, the porous matrix was gradually compressed by multiple passes through the rolling press, each time reducing the distance between the rollers from an initial of about 10 mm to the desired thickness. The effect of compression on the characteristics of obtained compressed mucoadhesive patches are shown in Table 3 and FIG. 5.

TABLE 3

The characteristics of the mucoadhesive patches before and after compression.

| Sl. No. | Thickness of patch (mm) | Compression cycle | Density (g/ml) | Tensile strength (N/mm²) | Swelling behaviour in Krebs Ringer Buffer (KRB) |
|---|---|---|---|---|---|
| 1 | 10 | 0 (uncompressed) | 0.035 | 37.4 ± 2.1 | Immediately swells to 1.5x |
| 2 | 4.89 ± 0.29 | 1 | 0.072 | 41.7 ± 3.7 | Immediately swells to 1.5x |
| 3 | 1.95 ± 0.14 | 2 | 0.179 | 49.5 ± 7.1 | Slowly swells to 1.2x |
| 4 | 0.29 ± 0.11 | 3 | 1.104 | 60.9 ± 9.4 | Doesn't swell, slowly turns into adhesive gel. |

Table 3 shows the parameters such as thickness of patch, compression cycle, density, tensile strength and swelling behavior in KRB employed in the present compression process confirm the achievement of desired properties of compressed mucoadhesive patches.

Example 3: Preparation of Mucoadhesive Powder

The fine powder of the compressed chitosan patch was prepared using a cryogenic ball mill (FIG. 10). The compressed patch was cut into small pieces of about 1 to 10 mm size. These pieces were then placed in the grinding jar of a bench top cryogenic-ball mill. The sample was cooled to −196° C. using liquid nitrogen and the mill was run at 500 rpm for 1 min, 5 min and 10 min. The average particle size was between 5 μm to 100 μm. The final particle size was dependent on the milling duration, the average particle sizes and uniformity are mentioned in Table 4 below.

TABLE 4

The average particle size and distribution of cryo-milled particles of compressed patches

| Milling duration | Mean size (d, μm) | Size distribution (min to max) |
|---|---|---|
| 1 min | 90.9 ± 23.5 | 56 μm to 134 μm |
| 5 min | 32.7 ± 18.4 | 20 μm to 76 μm |
| 10 min | 8.5 ± 3.8 | 3 μm to 15 μm |

Table 4 shows the average particle size and distribution of cryo-milled particles of compressed patches confirm the achievement of desired properties of compressed patches.

Example 4: Preparation and Characterization of Drug-Loaded Mucoadhesive Patches by Pre-Loading Method Drug-loaded patches were prepared by dissolving a water-soluble model drug (paracetamol, about 0.5 to 2% w/w) in dilute acetic acid solution (0.75% w/w) with chitosan (2% w/w). The solution was then used to prepare the paracetamol-loaded porous matrices of chitosan, as per the example 1. The obtained matrix was then compressed to a thin patch, as per the example 2. The patch is referred to as Patch 01 in FIG. 6. Other variants of the drug loaded patch were prepared by combining an impermeable backing layer (Patch 02) or sandwiching the drug-containing layer between the backing layer and drug-free patch (Patch 03), as shown in FIG. 6.

The unidirectional drug release properties of these patches were evaluated in a Kreb's ringer buffer at about pH 6.8 to simulate conditions in oral cavity. The patches were held in horizontal diffusion cell with backing layer facing the donor compartment. The donor and receiver compartments were filled with the release media Kreb's Ringer buffer pH 6.8 and samples were withdrawn from the receiver compartment at predetermined time intervals. At the end of the study all samples were analyzed using UV spectrophotometer. The results obtained are depicted in FIG. 8, wherein the Patches 01-03 show slow release of the drug in the receiver compartment, indicating its suitability for sustained drug delivery.

Example 5: Preparation and Characterization of Drug-Loaded Patches by Post-Loading Method The post-loading method of drug loading involves treating the drug-free porous matrix of chitosan with a solution of desired drug. This method is suitable for compounds which are insoluble or unstable in the acidic chitosan solution. In this study, for exemplification, chlorhexidine was selected as a model drug, which is not sufficiently stable at acidic conditions.

The drug-free sponges of chitosan were prepared as described in Example 1. The sponges were cut into pieces of 1 $cm^2$ discs and were soaked in ethanolic solution of the model drug (chlorhexidine). The drug-loaded sponges were then taken out and air dried at room temperature of about 25° C. until the sponge is completely dried. The drug-containing sponges were then compressed as described in Example 2 to obtain the post-loaded drug-loaded patches. The method was optimized for the initial drug concentration and incubation time to achieve optimum drug-loading efficiency. The drug-loading efficiency was estimated by extracting the drug from the patches and quantifying it using a UV-spectrophotometer.

Table 5, shows the effect of drug concentration and incubation time on the drug content of the patches. The internal structure of post-loaded drug-containing patches before and after compression were examined using scanning electron microscopy (FIG. 7). As shown in FIGS. 7 A and B, the pore size of the drug-containing matrix was slightly smaller than the drug-free matrix (FIG. 3). After compression, the porous matrix had a closed pore structure (FIGS. 7 C and D), and the side view clearly showed multiple lamellas were stacked, but did not fuse together (FIG. 7 C). This unique arrangement of the lamellas allows for the enhanced mucoadhesion and sustained drug release even in the patches prepared using post-loading method.

The in-vitro drug release of the post-loaded drug containing patches was evaluated in Krebs Ringer buffer as described in example-4. The results indicated that the drug release kinetics can be controlled by varying the initial drug content of the patches. After a burst release for first 2 hours, a sustained release was observed for up to 24 hours. The drug release was further modified by preparing multi-layered patches as shown in FIG. 6.

Table 5 shows the drug concentration and incubation time employed in the post-loading method and confirms the achievement of desired properties of the post-loaded drug-containing patches.

TABLE 5

The effect of drug concentration and incubation time on the drug content in post-loaded patches.

| Drug concentration | Effect of incubation time on drug content (mg/$cm^2$) | | |
|---|---|---|---|
| | 30 min | 60 min | 120 min |
| 1% w/v | 0.65 ± 0.28 mg | 0.86 ± 0.41 mg | 1.31 ± 0.39 mg |
| 2.5% w/v | 1.42 ± 0.53 mg | 1.92 ± 0.65 mg | 2.25 ± 0.95 mg |
| 5% w/v | 2.88 ± 0.71 mg | 3.74 ± 0.84 mg | 4.12 ± 0.62 mg |

The effect of drug concentration and incubation time on the drug content in post-loaded patches are shown in the table 5 which confirm the achievement of desired properties of the drug-loaded patches.

Example 6: In Vitro Mucoadhesion and Residence Time Study

Performance of mucoadhesive drug delivery system intended to remain at the absorption site for prolonged duration was evaluated. Esophageal mucosa was separated from the adhering connective tissue and dissected into about 50×50 mm sized pieces. The dissected mucosa was fixed on an inclined support platform (about 30° angle) with apical surface facing upward. The mucosa was continuously hydrated with artificial saliva (about 0.5% mucin in PBS pH 7.0), at a rate of about 10 mL/min using an infusion set. The samples (mucoadhesive preparation patch/drug loaded patch and mucoadhesive powders showing desired properties as described in examples 2, and 4-5) were applied on the tissue by gently pressing the preparations on to the mucosal surface with the index finger for about 30 sec. The ex-vivo residence time was determined by recording the duration of displacement from the adhesion site (FIG. 9).

The mucoadhesion force was determined using esophageal mucosa as a substrate. The substrate was mounted on a flat platform and held in place using acrylate-glue. The mucoadhesive patches (2×2 cm$^2$) were placed on the mucosa and compressed for 30 seconds to achieve mucoadhesion. The top of patch was then adhered to another platform with a double-sided tape and both platforms were mounted in a tensile strength testing machine. The platforms were separated and the separation force of patch from mucosa was noted down as the mucoadhesive strength of patches. Due to the limitation of device and sample holder, adhesive strength of powders could not be measured. Table 6 displays the mucoadhesion force and residence time of various preparations.

The drug-free patch showed a higher mucoadhesive strength than the drug containing patches. However, the ex-vivo mucosal residence time was similar for all preparations. This indicated that, although the mucoadhesive force was slightly lower in drug-containing patches it was sufficient to provide a prolonged mucoadhesion in the conditions simulating the mucosa.

TABLE 6

The mucoadhesive force and ex-vivo mucosal residence time of various preparations.

| Preparation | Drug content/ patch. | Mucoadhesion force (N) | Ex vivo residence duration (h) |
| --- | --- | --- | --- |
| Drug-free patch | 0 | 1.53 ± 0.02 | >12 h |
| Paracetamol-loaded patches | 5 mg | 1.41 ± 0.01 | >12 h |
|  | 10 mg | 1.23 ± 0.02 | >12 h |
|  | 20 mg | 0.97 ± 0.03 | >12 h |
| Chlorhexidine-loaded patches | 1 mg | 1.53 ± 0.02 | >12 h |
|  | 2.5 mg | 1.53 ± 0.01 | >12 h |
|  | 5 mg | 1.28 ± 0.04 | >12 h |
| Drug- free mucoadhesive powder* | 0 | NA | >12 h |
| Paracetamol-loaded mucoadhesive powder* | 5 mg | NA | >12 h |
| Chlorhexidine-loaded mucoadhesive powder* | 5 mg | NA | >12 h |

*Mucoadhesive powders obtained by cryo milling of mucoadesive patches.

The mucoadhesive force and ex-vivo mucosal residence time of drug free and drug containing patches are shown in the table 6 which confirm the achievement of desired properties of the drug-containing patches.

We claim:

1. A mucoadhesive preparation comprising chitosan and an organic acid, wherein the mucoadhesive preparation is in a compressed form, and wherein the preparation contains about 46.1% w/w to about 86.8% w/w of chitosan, about 13.2% w/w to about 33.9% w/w of organic acid, and 0 to about 20% w/w of one or more drugs, wherein the chitosan is not chemically modified and wherein the compression is performed at a temperature ranging from about 0° C. to about 30° C. to obtain the mucoadhesive preparation.

2. The mucoadhesive preparation as claimed in claim 1, wherein the organic acid is selected from the group consisting of acetic acid, lactic acid, glycolic acid and citric acid; wherein the preparation contains about 75% w/w to 85% w/w of chitosan and about 15% w/w to about 25% w/w of organic acid.

3. The mucoadhesive preparation as claimed in claim 1, wherein the mucoadhesive preparation is in a form selected from the group consisting of patch, powder, spray, and matrix, or a combination thereof.

4. The mucoadhesive preparation as claimed in claim 1, wherein the mucoadhesive preparation comprises a drug; and wherein the mucoadhesive preparation is a pre-loaded drug mucoadhesive preparation or a post-loaded drug mucoadhesive preparation; and wherein the drug loaded mucoadhesive preparation is multi-layered; and wherein number of layers ranges from 2 to 3.

5. The mucoadhesive preparation as claimed in claim 3, wherein the thickness of the compressed patch ranges from about 10 μm to 1000 μm.

6. The mucoadhesive preparation as claimed in claim 1, wherein mucoadhesion time of the mucoadhesive preparation ranges from about 4 hours to 24 hours.

7. The mucoadhesive preparation as claimed in claim 1, wherein the density of the preparation ranges from about 0.05 g/cm3 to 0.5 g/cm3, porosity ranges from about 25% to 95% and pore size ranges from about 10 microns to 400 microns.

8. A method of obtaining the mucoadhesive preparation of claim 1, comprising steps of:
   a) contacting chitosan with organic acid, to obtain a chitosan solution and wherein the chitosan is not chemically modified;
   b) subjecting the chitosan solution to lyophilisation to obtain dry chitosan sponge; and
   c) compressing the dry chitosan sponge at a temperature ranging from about 0° C. to about 30° C. to obtain a mucoadhesive preparation, wherein the mucoadhesive preparation further comprises 0 to about 20% w/w of one or more drugs.

9. The method as claimed in claim 8, wherein the chitosan and the organic acid in step a) are stirred to obtain the chitosan solution, and wherein the pH of the solution is reduced to about pH 2.5 to 5.5 to obtain the chitosan solution in step a); and wherein the lyophilisation of chitosan solution in step b) involves freezing followed by primary drying and secondary drying; and wherein the compressing is carried out at a temperature ranging from about 15° C. to 25° C. in step c); and wherein the organic acid is selected from the group consisting of acetic acid, lactic acid, glycolic acid, citric acid and hydrochloric acid; wherein concentration of the chitosan in step a) ranges from about 0.5% w/w to 5% w/w and concentration of the organic acid ranges from about 0.5% w/w to 5% w/w; and wherein the chitosan is not chemically modified.

10. The method as claimed in claim 9, wherein the freezing is at temperature ranging from about −5° C. to −60° C. for time duration ranging from about 4 hours to 10 hours, the primary drying is at temperature ranging from about −40° C. to −5° C. for a time duration ranging from about 8 hours to 36 hours under a vacuum of about 50 mTorr to 250 mTorr, and the secondary drying is carried out at temperatures ranging from about 15° C. to 55° C. for a time duration ranging from about 2 hours to 10 hours.

11. The method as claimed in claim 8, wherein the dry chitosan is compressed into thin patches of thickness ranging from about 10 μm to 1000 μm using a bench top rolling press or hydraulic press at a temperature lower ranging from about 0° C. to about 30° C.

12. The method as claimed in claim 8, wherein the chitosan patch can further be prepared into a fine powder having a particle size of about 1μm to 100 μm by grinding the chitosan patch at a temperature ranging from about −200° C. to −5° C.; and wherein the grinding is achieved by planetary ball mill, cryogenic ball mill, or grinding mill.

13. A drug delivery system for delivering a drug to a patient in a sustained and controlled manner, the system comprising the mucoadhesive preparation as claimed in claim 1, and comprising 1-20% w/w of one or more drugs.

14. The drug delivery system as claimed in claim 13, wherein the drug is administered in a therapeutically effective amount; and the mucoadhesion time of the drug delivery system ranges from about 4 hours to 13 hours.

15. A method of delivering one or more drug to a subject in need thereof, wherein the method comprises application of the drug delivery system as claimed in claim 13 on the mucosal surface of the subject.

16. The method as claimed in claim 15, wherein the drug is administered in a therapeutically effective amount; wherein the mucosal surface of the subject is selected from the group consisting of buccal, sublingual, pharyngeal, esophageal, gastro-intestinal, nasal, ophthalmic, vaginal and rectal mucosae or any combinations thereof; and wherein the mucoadhesive preparation comprising chitosan and drug remains adhered to the mucosal surfaces for at least 4 hours to 24 hours.

17. The method as claimed in claim 8, wherein a drug loading step is carried out prior to lyophilisation to obtain pre-loaded drug mucoadhesive preparation or after lyophilisation to obtain post-loaded drug mucoadhesive preparation; and wherein the drug loading is carried out by contacting the drug with the chitosan solution obtained in step a) or the mucoadhesive preparation obtained in step c).

* * * * *

UNITED STATES PATENT AND TRADEMARK OFFICE
CERTIFICATE OF CORRECTION

| | |
|---|---|
| PATENT NO. | : 11,491,107 B2 |
| APPLICATION NO. | : 16/347246 |
| DATED | : November 8, 2022 |
| INVENTOR(S) | : Leo Mavely, Kiran Sonaje and Indu A. G. |

It is certified that error appears in the above-identified patent and that said Letters Patent is hereby corrected as shown below:

In the Claims

Claim 14, Column 23, Line 23:
Please delete:
"system ranges from about 4 hours to 13 hours."
Please replace with:
system ranges from about 4 hours to 24 hours.

Signed and Sealed this
Sixteenth Day of May, 2023

Katherine Kelly Vidal
*Director of the United States Patent and Trademark Office*